(12) United States Patent
Potyrailo et al.

(10) Patent No.: US 6,362,006 B1
(45) Date of Patent: Mar. 26, 2002

(54) RAPID PARALLEL DETERMINATION OF NON-VOLATILE ANALYTES IN COMPLEX COMBINATORIAL SAMPLES

(75) Inventors: Radislav Alexandrovich Potyrailo, Niskayuna; John Patrick Lemmon, Delanson, both of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/561,004

(22) Filed: Apr. 28, 2000

Related U.S. Application Data (60) Provisional application No. 60/188,875, filed on Mar. 13, 2000.

(51) Int. Cl.[7] .............................................. G01N 21/64
(52) U.S. Cl. ...................... 436/131; 436/172; 436/177; 422/82.09
(58) Field of Search .................. 436/131, 164, 436/172, 177, 181; 250/458.1, 459.1; 422/82.07, 82.09

(56) References Cited

U.S. PATENT DOCUMENTS

| | | | |
|---|---|---|---|
| 4,677,079 A | * | 6/1987 | Langhals ..................... 436/164 |
| 4,759,210 A | | 7/1988 | Wohltjen |
| 5,244,813 A | * | 9/1993 | Walt et al. .................. 436/172 |
| 5,391,300 A | | 2/1995 | Webb et al. |
| 5,512,490 A | * | 4/1996 | Walt et al. .................. 436/171 |
| 5,606,008 A | | 2/1997 | Sakashita et al. |
| 5,621,522 A | | 4/1997 | Ewing et al. |
| 5,840,256 A | | 11/1998 | Demers et al. |
| 5,846,396 A | | 12/1998 | Zanzucchi et al. |
| 5,854,684 A | | 12/1998 | Stabile et al. |
| 6,022,943 A | | 2/2000 | Inoue et al. |
| 6,210,910 B1 | * | 4/2001 | Walt et al. .................. 435/7.32 |
| 6,266,459 B1 | * | 7/2001 | Walt et al. ..................... 385/12 |
| 6,271,042 B1 | * | 8/2001 | Watson, Jr. et al. ........ 436/172 |

OTHER PUBLICATIONS

Environ. Sci. Technol., Fiber–Optic Organic Vapor Sensor, Steven M. Barnard and David R. Walt, vol. 25, No. 7, pp. 1301–1304, 1991.

American Chemical Society, Solvatochromic Dyes as Solvent Polarity Indicators, Christian Reichardt, vol. 94, No. 8, pp. 2318–2359, 1994.

J. Chem. Soc., Chem. Commun., Covalent Immobilisation of Solvatochromic Dyes, David Crowther and Xiaoming Liu, p. 2445, 1995.

Chem. Mater., Probing the Microenvironment of Polymer–Impregnated Composite Glass Using Solvatochromic Dye, R. Gvishi, U. Narang, FV Bright and PN Prasad, vol. 7, pp 1703–1708, 1995.

Nature, *A Chemical–Detecting System Based on a Cross–Reactive Optical Sensor Array*, Todd A. Dickinson, Joel White, John S. Kauer and David R. Walt, vol. 382, Aug. 22, 1996.

The Proceedings of a Symposium Sponsored by Air & Waste Management Association, San Francisco, CA, Optical Remote Sensing for Environmental and Process Monitoring, Sep. 25–27, 1995.

(List continued on next page.)

*Primary Examiner*—Jeffrey Snay
(74) *Attorney, Agent, or Firm*—Noreen C. Johnson; Christian G. Cabou

(57) ABSTRACT

A method and apparatus for rapid parallel determination of non-volatile analytes in multiple samples is provided. The method utilizes analyte-enhanced fluorescence of a solvatochromic dye, and thus is not dependent on fluorescence of the analyte itself. An evaporation step removes volatile sample components that might otherwise interfere with analyte determination. The method is sensitive to a wide range of analyte concentrations and robust to variations in sample volume.

23 Claims, 6 Drawing Sheets

OTHER PUBLICATIONS

J. Agric. Food Chem., Determination of Bisphenol–A in Reusable Polycarbonate Food–Contact Plastics and Migration to Food–Simulating Liquids, JE Biles, TP McNeal, TH Begley and HC Hollifield, vol. 45, pp. 3541–3544, 1997.

Anal. Chem., Generating Sensor Diversity Through Combinatorial Polymer Synthesis, Todd A. Dickinson adn David R. Walt, vol. 69, pp 3413–3418, 1997.

Fresenius J. Anal. Chem., Use of the Original Silicone Cladding of an Optical Fiber as a Reagent–Immobilization Medium for Intrinsic Chemical Sensors, Radislav A. Potyrailo and Gary M. Hieftje, 364, pp 32–40, 1999.

Anal. Chem., Characterization of Reversed–Phase Liquid Chromatographic Stationary Phases Using Solvatochromism and Multivariate Curve Resolution, Shalini Nigam, Anna de Juan, Vickie Cui and Sarach C. Rutan, vol. 71, pp 5225–5234, 1999.

* cited by examiner

RAPID PARALLEL DETERMINATION OF NON-VOLATILE ANALYTES IN COMPLEX COMBINATORIAL SAMPLES

CROSS REFERENCE TO RELATED APPLICATIONS

This application claims priority to and the benefit of the filing date of Provisional Application Serial No. 60/188,875, filed Mar. 13, 2000, entitled "RAPID PARALLEL DETERMINATION OF NON-VOLATILE ANALYTES IN COMPLEX COMBINATORIAL SAMPLES".

BACKGROUND

The present invention relates to a method for rapid parallel detection of one or more analytes in a plurality of samples. In particular, the invention relates to a method for parallel detection of one or more non-volatile analytes in a plurality of samples, at least one of which comprises a volatile component.

Combinatorial techniques are being extended to diverse areas of chemical research. For example, combinatorial techniques can be used to identify and optimize catalysts and reaction conditions for polymerization reactions. However, the complexity of these reaction mixtures often complicates the quantitation of individual reactants, products, side-products or intermediates. In the synthesis of polycarbonates, current analytical measurements of the reactant bisphenol A (BPA) involve traditional separation techniques that are too time consuming where a large number of samples are involved (see, for example, J. E. Biles, T. P. McNeal, T. H. Begley and H. C. Hollifield, *Journal of Agricultural Food Chemistry*, volume 45, pages 3541–3544 (1997)).

Use of spectroscopic imaging can lead to increased sample throughput. With parallel spectroscopic imaging of large sample arrays, the measurement time is nearly independent of the number of samples. This advantage makes possible rapid analysis of even highly dense combinatorial arrays. U.S. Pat. No. 5,854,684 to Stabile et al. describes techniques for imaging sample arrays by a variety of spectroscopic techniques. However, the techniques described in this reference are unsuitable for determination of an analyte when other reaction components interfere with that determination.

Parallel fluorescence imaging provides low detection limits on variety of species that have native fluorescence. Unfortunately, the low fluorescence quantum yields of many analytes of interest, including BPA, preclude their direct detection. In addition, possible interferences from other reaction components (e.g., phenol) complicate reliable quantitation.

Polarity sensitive reagents (e.g., solvatochromic dyes) have been used for detection of volatile components and solvents of differing polarity. For example, a polarity sensitive reagent has been immobilized onto an analyte-permeable membrane to form a sensor (see, for example, S. M. Barnard and D. R. Walt, *Environmental Science and Technology*, volume 25, pages 1301–1304 (1991); and R. A. Potyrailo and G. M. Hieftje, *Fresenius' Journal of Analytical Chemistry*, volume 364, pages 32–40 (1999)). A known limitation of this detection approach is the low selectivity of measurements in complex multi-component solutions or gas mixtures. This limitation can be addressed by using an array of sensors with diverse intrinsic polarities (see, for example, T. A. Dickinson, J. White, J. S. Kauer and D. R. Walt, *Nature*, volume 382, pages 697–700 (1996); and T. A. Dickinson, D. R. Walt, J. White and J. S. Kauer, *Analytical Chemistry*, volume 69, pages 3413–3418 (1997)). However, the use of separate sensor array for each of the combinatorial samples significantly complicates the measurement system.

As such, there remains a long felt, yet unappeased need for a method of rapidly determining various properties of poorly fluorescing analytes when dealing with a large number of multi-component samples.

SUMMARY OF THE INVENTION

Accordingly, the present invention is directed to a system and method utilizing analyte-modulated fluorescence of a solvatochromic dye on an inert sorbent material. In one embodiment, the method comprises providing a plurality of analytical samples comprising at least one non-volatile analyte for which the concentration is to be determined and at least one volatile component; providing an analytical matrix comprising a plurality of spatially differentiated analytical sites, each site comprising a sorbent material and a solvatochromic dye; delivering a known amount of each analytical sample onto at least one unique analytical site; subjecting the matrix to conditions effective to substantially evaporate the at least one volatile component of the analytical samples; irradiating a plurality of the analytical sites on the matrix with a first selected wavelength range; detecting a spectroscopic characteristic of the solvatochromic dye from each analytical site on the matrix with a second selected wavelength range; and determining a concentration of the non-volatile analyte at each analytical site based on the spectroscopic characteristic of the solvatochromic dye.

DETAILED DESCRIPTION OF PREFERRED EMBODIMENTS

Rapid parallel detection of a poorly fluorescing analyte in a plurality of complex solutions or reaction mixtures can be accomplished by a method comprising: providing a plurality of analytical samples comprising at least one non-volatile analyte for which the concentration is to be determined and at least one volatile component; providing an analytical matrix comprising a plurality of spatially differentiated analytical sites, each site comprising a sorbent material and a solvatochromic dye; delivering a known amount of each analytical sample onto at least one unique analytical site; subjecting the matrix to conditions effective to substantially evaporate the at least one volatile component of the analytical samples; irradiating all analytical sites on the matrix with a first selected wavelength range; detecting a spectroscopic characteristic of the solvatochromic dye from each analytical site on the matrix with a second selected wavelength range; and determining a concentration of the non-volatile analyte at each analytical site based on the spectroscopic characteristic of the solvatochromic dye.

The method provides a plurality of analytical samples comprising at least one non-volatile analyte for which the concentration is to be determined and at least one volatile component. In this context, a non-volatile analyte is an analyte that is a liquid at 25° C. and has a boiling point greater than 150° C. or an analyte that is a solid at 25° C. and has a vapor pressure of less than 0.01 torr at 25° C. A volatile component is a component that is a liquid at 25° C. and has a boiling point less than 140° C. or a component that is a solid at 25° C. and has a vapor pressure greater than 0.02 torr at 25° C.

The analytical samples comprise a solvent that may be, e.g., aqueous, organic, mixed organic, or any miscible mixture of aqueous and organic solvents. Preferred analytical samples include polycarbonate polymerization reaction mixtures in which the analyte is a dihydric phenol. In addition to the dihydric phenol, the mixtures may additionally comprise one or more of a diaryl carbonate, a carbonyl halide (e.g., phosgene), a polycarbonate, a reaction catalyst, reaction by-products (e.g., phenol), water, and one or more organic solvents (e.g., acetone, dichloromethane or acetonitrile). Art recognized polycarbonate polymerization reactants, products, catalysts and solvents are described in, for example, U.S. Pat. No. 5,606,008 to Sakashita et al. A preferred dihydric phenol analyte is 2,2-bis(4-hydroxyphenyl)propane (bisphenol A; BPA; CAS Registry No. 80-05-7).

The analytical sample may comprise more than one analyte. In such cases, the method can comprise at least two evaporation steps: the first to remove volatile components (leaving both analytes), and the second to remove the more volatile of the two analytes. For example, the analytical sample can be a mixture of phenol, acetone, water, BPA and diphenylcarbonate (DPC). BPA and DPC are common starting components for production of polycarbonate. The phenol and acetone (and, depending on the sorbent material used, the water) can be removed by evaporation, allowing fluorescence detection indicative of the joint presence of BPA and DPC. A second evaporation step can then be carried out to substantially remove the BPA (boiling point 220° C.), allowing detection of the DPC alone (boiling point 301° C.), and, by subtraction, determination of the BPA alone.

The analytical matrix can comprise a plurality of spatially differentiated analytical sites, each site having a sorbent material and a solvatochromic dye. The sorbent material can be chosen from any suitable material effective for solution of the solvatochromic dye and the analyte, and the selection of a sorbent material can, of course, depend on the chemical natures of the solvatochromic dye and the analyte. Exemplary sorbent materials are well known in the art and include activated carbon, silica, alumina, diatomaceous earth, zeolite molecular sieves, carbon molecular sieves, metallic particles, semiconductor particles, dielectric particles, polymeric sorbents, and mixtures comprising at least one of the foregoing. The polymeric sorbents may include natural rubber and polymers formed at least in part from the polymerization of dienes, polyethylenes and polypropylenes, elastomeric polyesters, alkenyl aromatic resins, silicones, silicone polyimides, polyurethanes, polyphenylene ethers, and the like. The sorbents may have particle sizes ranging from about 1 nanometer to about 1 millimeter. Chemically modified sorbents are expressly included (for example, a silica gel with a hydrophobic coating of covalently attached $C_{18}$ carbon chains). Specific sorbent materials are well known to those of ordinary skill in the art in connection with, for example, gas chromatography and liquid chromatography techniques. Illustrative sorbent materials include the poly(ethylene oxide) materials having weight average molecular weights greater than 1,000,000, available from Aldrich; the poly(2,6-diphenyl-p-phenylene ether) materials under the trademark TENAX® available through Alltech Associates, Inc.; the graphitized carbon-based adsorbents available under the tradenames CARBOPACK™ and CARBOTRAP™ through Alltech Associates; the carbon molecular sieves available under the tradenames CARBOXEN™ and CARBOSIEVE™ through Supelco Incorporated, Bellefonte, Pa.; the family of styrene divinyl benzene polymers, ethyl vinyl and divinyl benzene polymers, vinyl pyrrolidone polymers, and vinyl pyridine polymers available under the tradename PORAPAK™ through Alltech Associates, Inc.; the diatomite-based and polymer-based (styrene divinyl benzene polymers, cross-linked polystyrene, polyacrylonitrile and cross-linked acrylic esters) support materials and adsorbents for chromatography available under the trademark CHROMOSORB® through Aldrich Chemicals; and the treated diatomaceous earth under the trademark GAS-CHROM® available through Alltech Associates, Inc. When the analyte is BPA, preferred sorbent materials include the diatomaceous earth material sold as CHROMOSORB® W-HP by Aldrich Chemicals, the treated diatomaceous earth material sold as GAS-CHROM® Q by Alltech, and the like. Mixtures of two or more sorbent materials may be used, and additional ingredients, Such as binders and surfactants, may optionally be added to the sorbent material. Different surfactants can be used to control liquid penetration into the sorbent material. These can include anionic, cationic and nonionic surfactants.

The amount of sorbent material employed per analytical site may vary widely and need only be effective to accommodate the delivered amount of analytical sample without exceeding saturation. The amount of sorbent material will therefore vary roughly in proportion to the known amount of analytical sample. Generally, each analytical site will include about 1 microgram to about 100 milligrams of sorbent material.

The above-mentioned sorbent material is intimately admixed with a solvatochromic dye. Solvatochromic dyes are dyes having spectroscopic characteristics (e.g., absorption, fluorescence, phosphorescence) in the ultraviolet/visible/near-infrared spectrum that are influenced by the surrounding medium. Both the wavelength-dependence and the intensity of a dye's spectroscopic characteristics are typically affected. The solvatochromic dye suitable for use with the above-mentioned sorbent materials may be any known solvatochromic dye. Solvatochromic dyes have been extensively reviewed in, for example, C. Reichardt, *Chemical Reviews*, volume 94, pages 2319–2358

(1994); C. Reichardt, S. Asharin-Fard, A. Blum, M. Eschner, A.-M. Mehranpour, P. Milart, T. Nein, G. Schaefer, and M. Wilk, *Pure and Applied Chemistry*, volume 65, no. 12, pages 2593–601 (1993); E. Buncel and S. Rajagopal, *Accounts of Chemical Research*, volume 23, no. 7, pages 226–31 (1990). Preferred fluorescent solvatochromic dyes have a fluorescence quantum yield of greater than about 0.01.

Other characteristics of the dyes include positive or negative solvatochromic which corresponds to the bathochromic and hypsochromic shifts, respectively of the emission band with increasing solvent polarity. In addition to the solvent-induced spectral shifts of the emission spectra, some dyes exhibit the solvent-dependent ratio of emission intensities of two fluorescence bands. One such solvatochromic dye is pyrene.

Where the analyte is BPA, preferred solvatochromic dyes include 4-dicyanmethylene-2-methyl-6-(p-dimethylaminostyryl)-4H-pyran (DCM; CAS Registry No. 51325-91-8); 6-propionyl-2-(dimethylamino)naphthalene (PRODAN; CAS Registry No. 70504-01-7); 9-(diethylamino)-5H-benzo[a]phenoxazin-5-one (Nile Red; CAS Registry No. 7385-67-3); phenol blue; stilbazolium dyes; coumarin dyes; ketocyanine dyes, including CAS Registry No. 63285-01-8; Reichardt's dyes including Reichardt's Betaine dye (2,6-diphenyl-4-(2,4,6-triphenylpyridinio)phenolate; CAS Registry No. 10081-39-7); merocyanine dyes, including merocyanine 540 (CAS Registry No. 62796-23-0); so-called $\pi^*$ dyes, including N,N-dimethyl-4-nitroaniline (NDMNA; CAS Registry No. 100-23-2) and N-methyl-2-nitroaniline (NM2NA; CAS Registry No. 612-28-2); and the like.

Other preferred solvatochromic dyes include 4-dicyanmethylene-2-methyl-6-(p-dimethylaminostyryl)-4H-pyran (DCM; CAS Registry No. 51325-91-8); 6-propionyl-2-(dimethylamino)naphthalene (PRODAN; CAS Registry No. 70504-01-7); and 9-(diethylamino)-5H-benzo[a]phenoxazin-5-one (Nile Red; CAS Registry No. 7385-67-3).

The solvatochromic dye is employed in a quantity effective to provide a detectable spectroscopic signal from each analytical site. This amount will depend on the dye's molecular weight and spectroscopic characteristics, as well as the amount of analytical sample to be added to each analytical site. Generally, each analytical site may comprise about 0.1 nanogram to about 1 milligram of solvatochromic dye. The sorbent material and the solvatochromic dye may be combined by any method capable of achieving the desired distribution of dye on the surface of the sorbent material particles. When uniform distribution of the dye on the surface of the sorbent material is desired, the dye may be dissolved in a suitable volatile solvent and the resulting solution added to the particulate (e.g., powdered) sorbent material. The resulting mixture is thoroughly stirred or otherwise mixed to evenly distribute the solvatochromic dye about the surface of the sorbent material. The volatile solvent is then removed, e.g., under vacuum, to yield sorbent material with adsorbed solvatochromic dye. Alternatively, when it is desired to distribute the dye preferentially to the top surface of the sorbent material, a solution of the dye may simply be added to the top surface of an analytical site that has been pre-packed with sorbent material. In yet another alternative, the dye may be covalently linked to the sorbent (see, for example, D. Crowther and X. Liu, *Journal of the Chemical Society, Chemical Communications*, page 2445 (1995)).

The analytical matrix is prepared so as to provide a plurality of spatially differentiated analytical sites. For example, a portion of dyed sorbent material may be distributed into each well of a 96-, 384-, or 1536-well plate. These art-recognized plates and related plates are commercially available. However, custom made plates can be used as well. The exact number of analytical sites may vary widely, from two to about one million or more sites. For example, U.S. Pat. No. 5,854,684 to Stabile et al. describes analytical matrices comprising at least one million sites arranged in a density of at least about 10 sites per square centimeter, and U.S. Pat. No. 5,840,246 to Demers et al. provides details for a 7.25 square inch analytical matrix comprising 99,856 sites. In an alternative embodiment, the analytical sites are of uniform geometry and are uniformly distributed throughout all or a portion of the analytical matrix. In another alternative embodiment, the dye and sorbent material are distributed uniformly about an area of the analytical matrix, and spatial differentiation of analytical sites is provided by delivery of analytical samples to spatially differentiated sites within the uniformly distributed dye and sorbent material.

Delivery of a known amount of each analytical sample onto at least one unique analytical site may be accomplished by a sample loader capable of accurately and reproducibly delivering a known amount, where the known amount is expressed in dimensions of mass or volume. Use of the term "unique analytical site" is meant to convey that only one analytical sample is transferred to a given analytical site. Suitable delivery methods include microvolume syringes, peristaltic pumps, electrode-based micropumps (such as those described in U.S. Pat. No. 5,846,396 to Zanzucchi et al.), spraying, and piezoelectric pumps (such as those used in ink-jet printing). In a preferred embodiment, delivery is by a multi-channel syringe array, such as the eight-channel 10 microliter gel syringe array, available as part number 009998 from SGE, Inc. The known amount may be the same or different for various analytical samples. Also, when the same analytical sample is delivered onto more than one analytical site, the known amount of the sample may be the same or different between/among the multiple sites. In a preferred embodiment, the same known amount of each analytical sample is delivered onto at least two, more preferably at least three analytical sites, allowing the analyte concentration for a single analytical sample to be determined by using spectroscopic responses from multiple analytical sites. In general, the known amount of analytical sample is about 1 picoliter to about 1 milliliter. Preferred known amounts will depend on the application and on the delivery method. For example, analytical matrices with high analytical site densities may use volumes of about 1 to about 1000 picoliters, delivered, for example, by a piezoelectric pump. Analytical matrices with fewer analytical sites and lower analytical site densities may use volumes of 1 to 100 microliters, delivered, for example, by a multichannel syringe pump. Where the analyte is BPA, the known amount of analytical sample is about 1 microliter to about 100 microliters, preferably about 1 to about 50 microliters.

In one embodiment, hereafter referred to as "mass-independent analysis", the analytical sample, once added to the analytical site, interacts with the dye and sorbent material in such a way that the spectroscopic characteristics of the top surface of the analytical site are dependent on the analyte concentration but effectively independent of the analytical sample volume added to the analytical site. Although the claimed invention is not limited by any theory posited herein, the inventors believe that as the analytical sample volume increases, the analytical sample and the analyte contained therein penetrate deeper into the dye and sorbent material, but the amount of analyte retained on the top surface of the analytical site is essentially unaffected. The mass-independence of sample volume is observed as long as the analytical sample volume is large enough to wet a minimum surface area of the top of the analytical site and yet not so large as to saturate the dye and sorbent material. While this mass-independent method does not require any special techniques to sample fluorescence from the top layer, it is preferred to have a non-transparent, highly scattering surface in order to generate fluorescence from the top layer and to prevent excitation of fluorescence and emission from the deeper layers of sorbent material.

This mass-independent analysis can be desirable because determination of analyte concentration typically requires only a very small amount of analytical sample, and, consequently, the results are independent of substantial variations in amount of the analytical sample delivered to the analytical site.

While the method has been described in terms of adding a single analytical solution to each analytical site, it is expressly contemplated to combine more than one solution prior to analysis. For example, by adding two or more reagent solutions to each analytical site, the site can function as a reaction cell. In this case, the solutions may be combined and the reaction conduction prior to the addition of the sorbent material and solvatochromic dye. An art-recognized method of delivering reagents to microscale reaction vessels is described in U.S. Pat. No. 5,846,396 to Zanzucchi et al.

Once the analytical samples have been delivered onto the analytical matrix, the matrix is subjected to conditions effective to substantially evaporate at least one component of at least one of the analytical samples. Substantial evaporation of a component is defined as reduction of the original concentration of the component by at least about 80%. It is preferred to reduce the concentration by at least about 90%, and more preferred to reduce the concentration by at least about 95%. The evaporative conditions will vary depending on the component to be removed, from leaving the matrix at ambient temperature and pressure for a few minutes, for example, to the use of one or more of elevated temperatures, reduced pressures, atmosphere exchange, infrared radiation, microwave radiation, extended times, and the like. The evaporation conditions are adjusted to avoid driving off (e.g., evaporating or subliming) or chemically reacting the analyte, the solvatochromic dye or the sorbent material. Where the analyte is BPA, the evaporative conditions are preferably effective to substantially evaporate at least one of acetone, acetonitrile, phenol and water, without significantly affecting the concentration of BPA. Typically, these conditions are quite mild, involving ambient temperature and ambient or slightly reduced pressures (i.e., pressures of 1 to 760 torr).

Parallel fluorescence determination of the analyte concentration at each analytical site requires illumination of a plurality of analytical sites on the matrix with a first selected wavelength range $\lambda_1-\lambda_2$ and detection at a second selected wavelength range $\lambda_3-\lambda_4$ which is bathochromically displaced from $\lambda_1-\lambda_2$. The choice of wavelength values $\lambda_1$, $\lambda_2$, $\lambda_3$ and $\lambda_4$ will depend on the choice of solvatochromic dye and sorbent material as well as the sensitivity of the detector. The bandwidths defined by $\lambda_1-\lambda_2$ and $\lambda_3-\lambda_4$ can independently be as narrow as a fraction of a nanometer or as wide as several tens of nanometers. Typically, a bandwidth of about 0.1 to about 25 nm is used for irradiation and a bandwidth of about 1 to about 100 nm is used for detection. The selection of irradiation and detection wavelengths will depend on the analyte, solvatochromic dye, and sorbent material. For example, as described in detail below, sensitive detection of the analyte BPA using the solvatochromic dye 4-dicyanmethylene-2-methyl-6-(p-dimethylaminostyryl)-4H-pyran on GAS CHROM® Q sorbent material was achieved using irradiation at 510±5 nm (i.e., 505–515 nm) and detection at 590±5 nm (i.e., 585–595 nm). (Bandwidth is expressed as a center wavelength plus/minus half-width at half maximum).

Detection can be accomplished with any suitable array detection device. Examples include a charge-coupled device (CCD), charge-injection device (CID), a photodiode array, or a photodetector array, all of which are readily commercially available. The array detection device preferably has sufficient resolution that each analytical site is uniquely imaged by at least one, preferably at least nine, more preferably at least 25 pixels. Raw data corresponding to detection of each analytical site may be stored temporarily in the detection device or immediately transferred to a computer.

Fluorescence characterization of the an analytical matrix is conducted at least after the evaporation step. For comparison purposes it may also be conducted before addition of the analytical samples to the analytical matrix, or after addition of the analytical samples to the analytical matrix but before evaporation. The latter method can be used when information about both volatile and non-volatile components is needed. Increased sensitivity may be achieved by extending times of continuous irradiation and detection, or by integrating results from multiple, temporally separated periods of irradiation and detection.

Once fluorescence characterization of the analytical matrix is complete, raw data corresponding to detection of each site may be transferred to or recalled from the computer and converted to the corresponding analyte concentrations. This conversion may be accomplished by a previously established look-up table or conversion function derived from calibration testing. In the case of an analytical sample being tested on more than one analytical site, results for each s site may be averaged or otherwise combined to generate an aggregate value and associated uncertainty using, common statistical techniques.

A variation of the method can be used to determine a suitable sorbent-dye pair for use in determination of a given analyte. In particular, the plurality of analytical sites can be used to survey the analyte sensitivity of combinations formed from a first series of sorbent materials and as second series of dyes, each series chosen to span values of one or more important parameters. For solvatochromic dyes, these parameters can include solubility, aggregation propensity and morphology, chemical composition, polarity, polarizability, hydrogen-bond accepting ability, hydrogen-bond donating ability, and the like. For sorbent materials, these parameters can include particle size, porosity, surface area, surface energy, wettability, molecular weight (for polymeric materials), nature of an counterions, and the like. Leaving a side ancillary considerations such as cost and availability, the optimum sorbent-dye combination will be the one having fluorescence characteristics strongly modulated by the presence of the analyte. While the dye's fluorescence emission can either be enhanced or diminished by the analyte, as long as the modulation is strong, it is preferred that the presence of the analyte enhances the dye's fluorescence emission. This is because diminished fluorescence in the presence of analyte is subject to more interferences. For example, signal decrease can be associated not only with the presence of analyte but also with the loss of dye, degradation of optics, and other factors unrelated to the analyte.

While the method has been described in terms of fluorescence spectroscopy, it will be understood that it can be easily be adapted to employ other spectroscopic techniques such as UV-visible absorbance (colorimetry), phosphorescence, chemiluminescence, infrared absorbance, Raman spectroscopy, and the like. Thus, depending on the spectroscopic technique employed, the solvatochromic dye need not be fluorescent.

Figure 1:
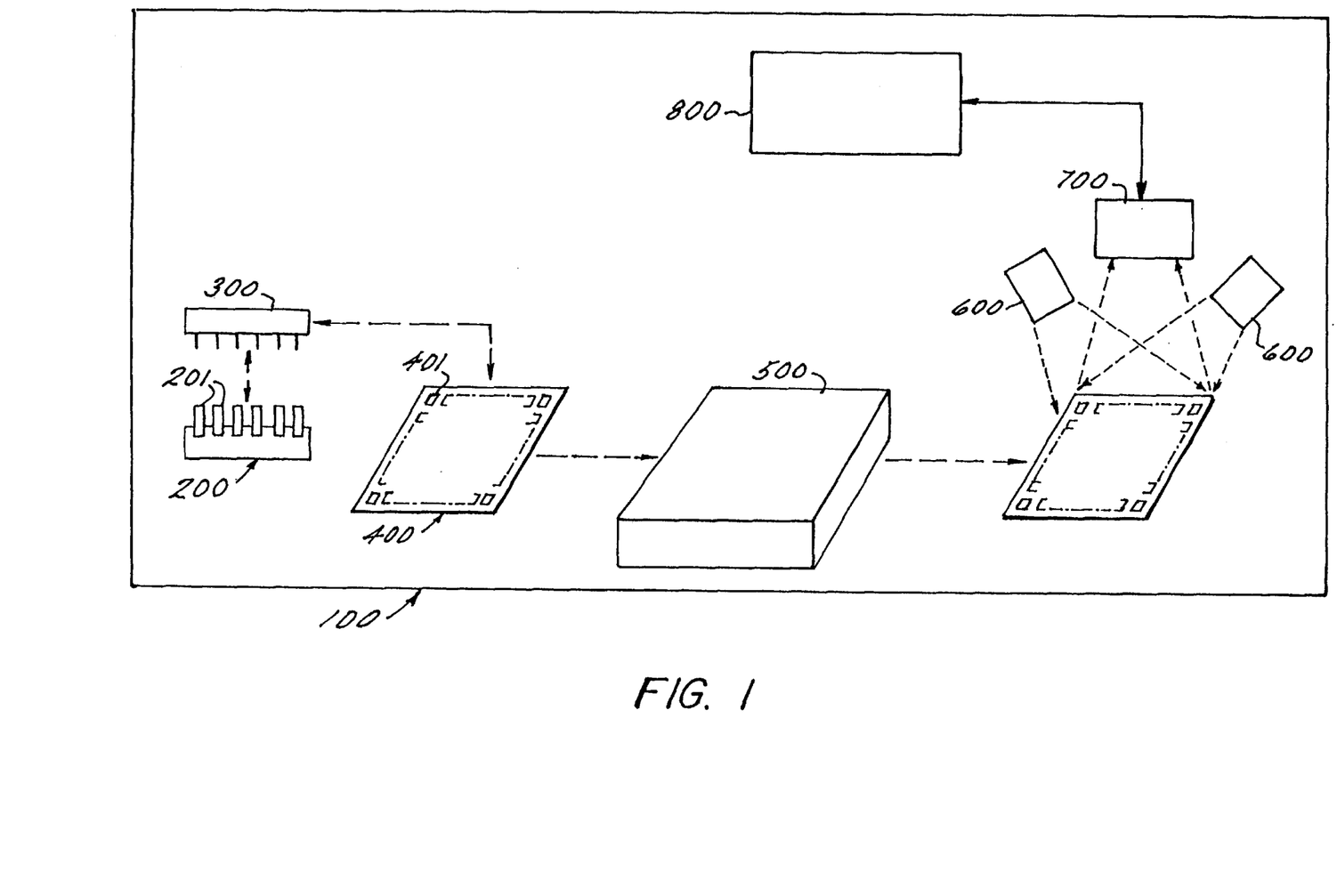
FIG. 1 is a block diagram of an apparatus for rapid parallel determination of a non-volatile analyte in a plurality of samples.

FIG. 1 illustrates an embodiment of an analytical system 100 for carrying out an embodiment of the present method. A plurality 200 of individual analytical samples 201 is provided. In operation, a sample loader 300 withdraws a portion of each analytical sample 201 and delivers a known amount of each sample to at least one unique analytical site 401 on an analytical matrix 400. Each analytical site 401 comprises a sorbent material and an analytical dye. Once the analytical samples have been delivered to the analytical matrix, the matrix is transferred to an evaporator 500, where one or more volatile components of the analytical samples are evaporated. The analytical matrix is then transferred to a station where fluorescence measurements are performed. The matrix is illuminated by one or more light sources 600, and the fluorescence emission from the matrix is detected by detector 700. The detector is connected to a computer 800 to which are transferred raw fluorescence data. Based on the raw fluorescence data and a calibration curve or look-up table determined earlier, computer 800 can calculate an analyte concentration for each analytical site on the matrix. Computer 800 may optionally responsively control one or more of sample loader 300, evaporator 500, light source 600, and detector 700.

The following examples are provided in order that those skilled in the art will be better able to understand and practice the present invention. These examples are intended to serve as illustrations and not as limitations of the present invention as defined in the claims herein.

EXAMPLE 1

The first example describes the experimental validation of the technique for determination of high concentrations of BPA (up to 16.5 weight percent) in multi-component solutions containing acetone, acetonitrile, phenol, and water.

For detection of BPA at high concentrations, an analytical matrix was prepared by imbibing a solvatochromic dye solution into a sorbent material. A 5×20 centimeter silica gel plate (Analtech 01031) was obtained with no added organic substances. Strong adhesion of the silica gel layer to the glass substrate was provided by a $CaSO_4 * \frac{1}{2} H_2O$ binder in the adsorbent formulation. The analytical matrix was prepared by immersing the silica gel plate for 5 minutes in a $10^{-5}$ mole/liter solution of 4-dicyanmethylene-2-methyl-6-(p-dimethylaminostyryl)-4H-pyran in chloroform.

A 10 microliter eight channel gel syringe array (SGE, Inc.) was used as a delivery array system for solutions containing BPA and phenol dissolved in acetone/acetonitrile/water solvent. Compositions of the calibration solutions are provided in Table 1.

TABLE 1

| Solution # | Acetonitrile (mL) | Acetone (mL) | $H_2O$ (µL) | Phenol (g) | BPA (g) | BPA conc. (wt. %) |
|---|---|---|---|---|---|---|
| 1 | 9.8 | 0.2 | 0 | 10 | 0 | 0 |
| 2 | 9.8 | 0.2 | 39 | 9.5 | 0.5 | 2.8 |
| 3 | 9.8 | 0.2 | 79 | 9 | 1 | 5.6 |

TABLE 1-continued

| Solution # | Acetonitrile (mL) | Acetone (mL) | $H_2O$ (µL) | Phenol (g) | BPA (g) | BPA conc. (wt. %) |
|---|---|---|---|---|---|---|
| 4 | 9.8 | 0.2 | 118 | 8.5 | 1.5 | 8.3 |
| 5 | 9.8 | 0.2 | 158 | 8 | 2 | 11.1 |
| 6 | 9.8 | 0.2 | 197 | 7.5 | 2.5 | 13.8 |
| 7 | 9.8 | 0.2 | 237 | 7 | 3 | 16.5 |

A two microliter volume of each solution per channel was deposited onto the surface of the analytical matrix. Volatile components of the analytical solutions were then allowed to evaporate by leaving the matrix at room temperature for several minutes. After evaporation the matrix was illuminated with a long wavelength (365-nm) UV lamp (Ultra-Violet Products, Inc. model B-100A) and imaged with a Kodak DC210 digital camera (1152×864 pixel sensor). Visual inspection of the resulting image indicated increasing fluorescence with increasing concentrations of BPA.

Figure 2:
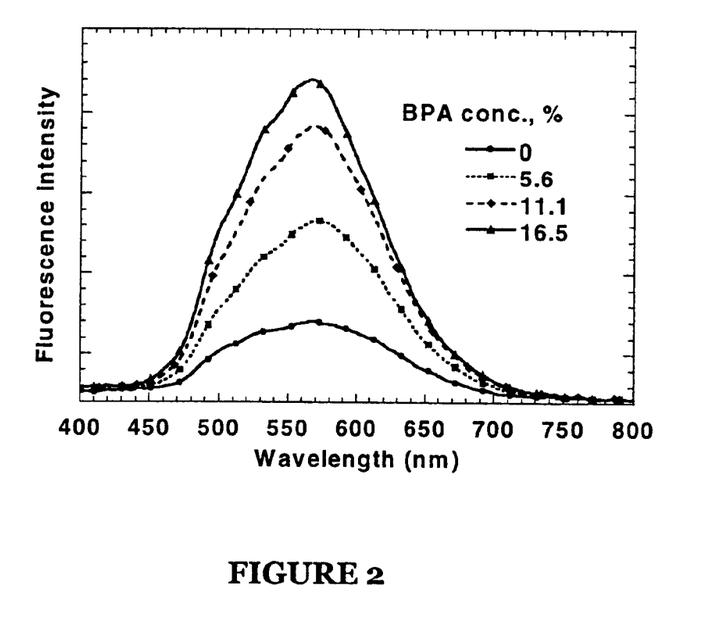
FIG. 2 shows fluorescence emission spectra of sensor materials exposed to various concentrations of bisphenol A (BPA).

Measurements of fluorescence spectra of 4-dicyanmethylene-2-methyl-6-(p-dimethylaminostyryl)-4H-pyran in the presence of varying concentrations of BPA were performed using a nitrogen laser as an excitation source and a portable spectrofluorometer (Ocean Optics, Inc., Dunedin, Fla., Model ST2000) to detect fluorescence emission. Excitation light from the laser (337.1 nm) was focused into one of the arms of a "six-around-one" bifurcated fiber-optic reflection probe (Ocean Optics, Inc., Model R400-7-UV/VIS). Emission light was collected from the sensor when the common end of the fiber-optic probe was positioned near the sensor. The second arm of the probe was coupled to the spectrofluorometer. Fluorescence spectra of the sensor material exposed to solutions 1, 3, 5 and 7 are presented in FIG. 2.

Figure 3:
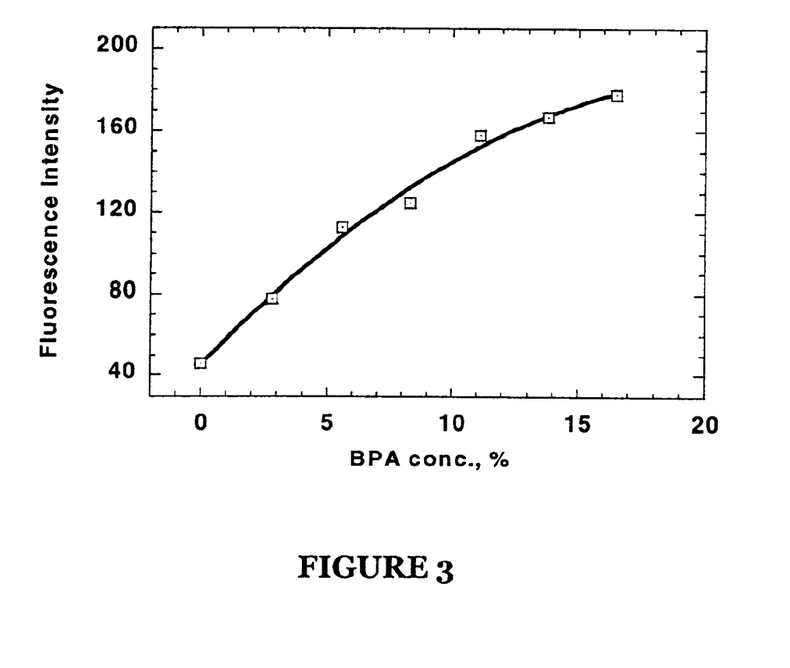
FIG. 3 shows a calibration curve relating fluorescence intensity of the sensor material upon exposure to high BPA concentrations.

Calibration was performed using the 575 nm emission from the set of calibration solutions described in Table 1. The fluorescence responses are plotted in FIG. 3. This example shows that it is possible to establish a calibration curve for samples BPA concentrations as high as 16.5 weight percent.

EXAMPLE 2

In this example, the analytical matrix was designed around the 96-well format, which is a common combinatorial system configuration. Imaging of the 96-well sensor array can was accomplished using instrumentation as described in Example 1. A variety of sorbent-dye combinations were surveyed to determine a sensitive system for detecting low concentrations of BPA.

The microenvironment of the solvatochromic dye can dramatically affect the performance of the analytical matrix by shifting its dynamic range, altering sensitivity, and even altering the direction of the signal change upon interactions with the analyte. Sorbent materials and solvatochromic dyes selected for the evaluation were as follows:

Sorbent Materials

I. Silicar silica gel, 200–425 mesh 60A (obtained from Mallinckrodt)

II. Poly(ethylene oxide), weight average molecular weight 5,000,000 (obtained from Aldrich)

III. 3% OV-275 on 80/100 CHROMOSORB® W-HP (obtained from Aldrich)

IV. GAS CHROM® Q, mesh size 100/120 (obtained from Alltech)

Solvatochromic Dyes

I. 4-Dicyanmethylene-2-methyl-6-(p-dimethylaminostyryl)-4H-pyran (obtained from Lambda Physik, Germany)

II. 6-propionyl-2-(dimethylamino)naphthalene (obtained from Molecular Probes, Eugene, Oreg.)

III. 9-(diethylamino)-5H-benzo[a]phenoxazin-5-one ("Nile Red"; obtained from Aldrich)

Solvatochromic dyes were dissolved in chloroform at a concentration of about $10^{-4}$ mole/liter. The immobilization matrices were packed into a glass 96-well plate. Each of the four sorbent materials was packed in sets of two rows, forming eight rows, A–H, of the matrix. About 100 microliters of a dye solution was added to each well of the microtiter plate. Three solvatochromic dye solutions were added in sets of four columns each, forming columns 1–12 of the matrix. Dye solutions were dried at room temperature under house vacuum (approximately 10 torr). A map of the matrix's analytical sites is presented in Table 2. For each site, the first Roman numeral represents the sorbent material and the second Roman numeral represents the solvatochromic dye.

TABLE 2

|   | 1 | 2 | 3 | 4 | 5 | 6 | 7 | 8 | 9 | 10 | 11 | 12 |
|---|---|---|---|---|---|---|---|---|---|----|----|----|
| A | I-I | I-I | I-I | I-I | I-II | I-II | I-II | I-II | I-III | I-III | I-III | I-III |
| B | I-I | I-I | I-I | I-I | I-II | I-II | I-II | I-II | I-III | I-III | I-III | I-III |
| C | II-I | II-I | II-I | II-I | II-II | II-II | II-II | II-II | II-III | II-III | II-III | II-III |
| D | II-I | II-I | II-I | II-I | II-II | II-II | II-II | II-II | II-III | II-III | II-III | II-III |
| E | III-I | III-I | III-I | III-I | III-II | III-II | III-II | III-II | III-III | III-III | III-III | III-III |
| F | III-I | III-I | III-I | III-I | III-II | III-II | III-II | III-II | III-III | III-III | III-III | III-III |
| G | IV-I | IV-I | IV-I | IV-I | IV-II | IV-II | IV-II | IV-II | IV-III | IV-III | IV-III | IV-III |
| H | IV-I | IV-I | IV-I | IV-I | IV-II | IV-II | IV-II | IV-II | IV-III | IV-III | IV-III | IV-III |

These reagent-matrix combinations provided 12 different sensing compositions. These sensor compositions were evaluated by adding 50 microliter portions of the BPA solutions and measuring the sensor response. For every dye, the first column of sensors was left blank (i.e., columns 1, 5 and 9). Fifty (50) microliters of a solution containing 0.9 phenol in 9.8 mL of acetonitrile and 0.2 mL of acetone was delivered to the second column for each dye (i.e., columns 2, 6 and 10). Fifty (50) microliters of a solution containing 0.1 g BPA, 0.9 g phenol in 9.8 mL of acetonitrile and 0.2 mL of acetone was delivered to the third and fourth columns for each dye (i.e., columns 3, 4, 7, 8, 11 and 12). The analytical matrix was exposed to house vacuum at room temperature for several minutes to evaporate acetone, phenol, acetonitrile and acetone.

After evaporation, the matrix was illuminated with ultraviolet light and imaged with a Kodak DC210 camera, as in Example 1. Visual inspection of the images indicated that the IV-I sensor had the dual advantages of increased fluorescence in the presence of BPA and a large change in fluorescence intensity as the concentration of BPA was varied.

EXAMPLE 3

For quantitative analysis, another plate was prepared combining dyes I and III with sorbent materials III and IV, as described above. Thus a matrix of four 3×6 element sensor arrays was fabricated on a single 96-well plate. The outline of the plate is presented in Table 3. Solutions used for BPA quantitation are listed in Table 4.

TABLE 3

|   | 1 | 2 | 3 | 4 | 5 | 6 | 7 | 8 | 9 | 10 | 11 | 12 |
|---|---|---|---|---|---|---|---|---|---|----|----|----|
| A | III-I | III-I | III-I | III-I | III-I | III-I | III-III | III-III | III-III | III-III | III-III | III-III |
| B | III-I | III-I | III-I | III-I | III-I | III-I | III-III | III-III | III-III | III-III | III-III | III-III |
| C | III-I | III-I | III-I | III-I | III-I | III-I | III-III | III-III | III-III | III-III | III-III | III-III |
| D |   |   |   |   |   |   |   |   |   |   |   |   |
| E |   |   |   |   |   |   |   |   |   |   |   |   |
| F | IV-I | IV-I | IV-I | IV-I | IV-I | IV-I | IV-III | IV-III | IV-III | IV-III | IV-III | IV-III |
| G | IV-I | IV-I | IV-I | IV-I | IV-I | IV-I | IV-III | IV-III | IV-III | IV-III | IV-III | IV-III |
| H | IV-I | IV-I | IV-I | IV-I | IV-I | IV-I | IV-III | IV-III | IV-III | IV-III | IV-III | IV-III |

TABLE 4

| Soln. no. | acetonitrile (mL) | acetone (mL) | phenol (g) | BPA (g) | BPA conc. (wt %) |
|---|---|---|---|---|---|
| 1 | 9.8 | 0.2 | 0.9 | 0 | 0.0 |
| 2 | 9.8 | 0.2 | 0.9 | 0.02 | 0.2 |
| 3 | 9.8 | 0.2 | 0.9 | 0.04 | 0.4 |
| 4 | 9.8 | 0.2 | 0.9 | 0.10 | 1 |

For the six columns of each sorbent-dye combination, no solution was added to the first and sixth columns (i.e., columns 1, 6, 7 and 12 received no solution). Calibration solutions 1–4 were delivered, respectively, to the second through fifth columns (i.e., solution 1 in columns 2 and 8; solution 2 in columns 3 and 9; solution 3 in columns 4 and 10; and solution 4 in columns 5 and 11). Columns of sensors of the 96 well plate were exposed to different concentrations of BPA dissolved in acetonitrile/acetone solution. Images were recorded under four conditions corresponding to pre- and post-evaporation, and white light and ultraviolet illumination. Visual inspection of the images suggested, first, that the fluorescence was markedly different before and after evaporation of the samples. This is an indication that evaporation is removing volatile species that would otherwise have interfered with BPA determination. Visual inspection also suggested that while the III-I and IV-I sensors both had enhanced fluorescence in the presence of BPA, the IV-I sensor showed the greater change in fluorescence intensity per change in BPA concentration.

Figure 4:
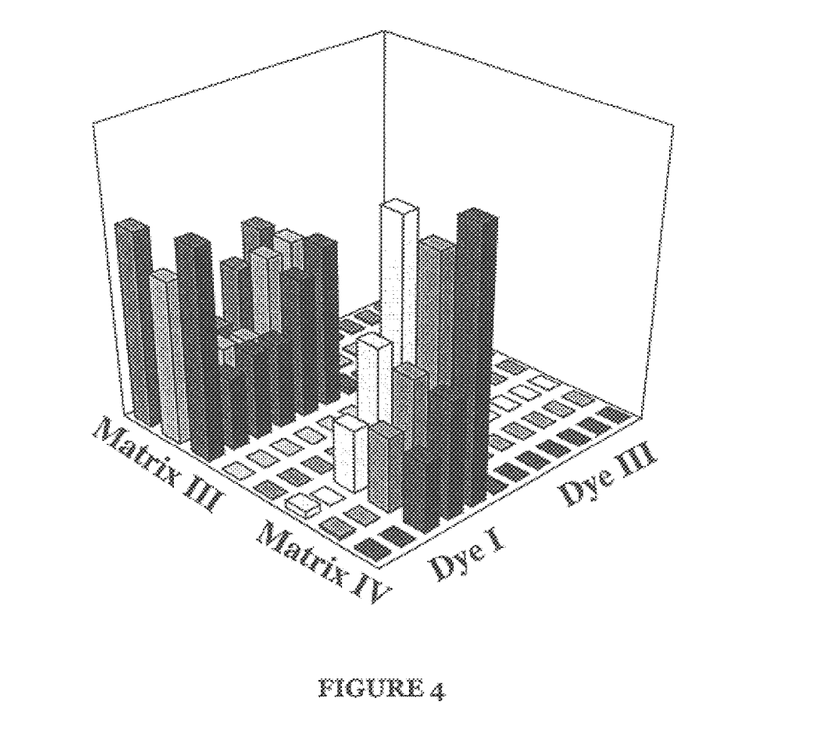
FIG. 4 shows a fluorescence map measured with 485 nm excitation and 538 nm emission; sorbent-dye combinations and BPA concentrations were varied.
Figure 5:
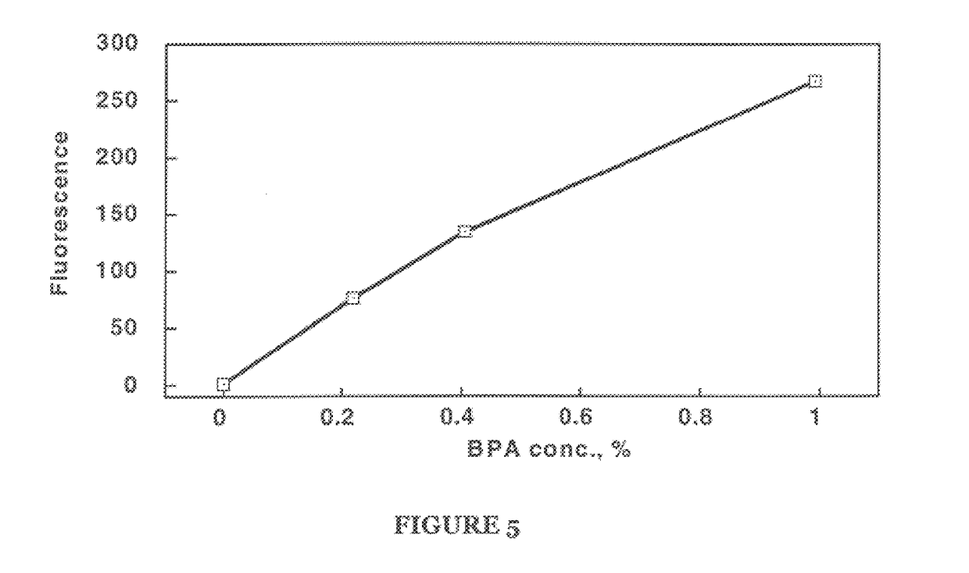
FIG. 5 shows a calibration curve relating fluorescence intensity of the sensor material upon exposure to low BPA concentrations.

Quantitative fluorescence determinations were performed for the IV-I sensor array using a microplate fluorometer (Fluoroskan II, Labsystems, Helsinki, Finland). The integration time for reading each of the wells in the plate was selected to be 0.1 second. The total measurement time of the 96-well array was less than 2 minutes. This time included 40 seconds for an autocalibration, 96-well microtiter, plate manipulation, and data storage and 60 seconds for the fluorescence measurements. FIG. 4 shows a typical fluorescence map measured with 485 nm excitation and 538 nm emission. Calibration curves were obtained at different excitation/emission conditions. A typical calibration curve in presented in FIG. 5. BPA detection limits, expressed in units of parts per million (ppm), are summarized in Table 5.

TABLE 5

| excitation wavelength (nm) | emission wavelength (nm) | BPA detection limit (ppm) |
| --- | --- | --- |
| 485 | 538 | 880 |
| 520 | 560 | 450 |
| 510 | 590 | 250 |

Quantitative analysis of fluorescence intensities confirmed that, for the conditions used in this experiment, the IV-I sensor combination is preferred for two reasons. First, the signal intensity increased with this sensor's exposure to BPA. Second, the IV-I sensor provided the largest signal chance in the presence of BPA. The intensity increase is a factor of primary importance, because, as mentioned above, signal decrease can be associated not only with the presence of analyte but also with the loss of dye, degradation of optics, and other factors unrelated to the analyte. Other sensors demonstrated either a decrease in intensity upon exposure to BPA or only slight signal change.

This example shows that a useful sensor for BPA can be prepared from a treated diatomaceous earth sorbent material and 4-dicyanmethylene-2-methyl-6-(p-dimethylaminostyryl)-4H-pyran dye. It also shows that the method can provide detection of low concentrations of BPA and further that the evaporation step removes materials that would otherwise influence the fluorescence measurements.

EXAMPLE 4

This example demonstrates rapid parallel determination of small analyte concentrations in a multitude of samples using quantitative fluorescence imaging. The extreme sensitivity of the method indicates that only a very small amount of sample (e.g., 2 microliters) may be needed for each analysis.

For detection of BPA, an analytical matrix was prepared by imbibing a solvatochromic dye solution into a sorbent material. A 5×10 centimeter silica gel plate (Analtech 01031) was used with no added organic substances. Strong adhesion of the silica gel layer to the glass substrate was provided by a $CaSO_4 * \frac{1}{2} H_2O$ binder in the adsorbent formulation. The analytical matrix was prepared by immersing the silica gel plate for 1 minute in a $10^{-4}$ mole/liter solution of 4-dicyanmethylene-2-methyl-6-(p-dimethylaminostyryl)-4HI-pyran in chloroform.

A 250 microliter eight channel electronic digital pipette (Rainin, Inc. model EDP2) was used as a delivery array system for solutions containing BPA and phenol dissolved in acetone/acetonitrile solvent. Calibration solutions were prepared as in Example 1 and contained 0, 0.028, 0.186, 0.276, and 0.53% of BPA by weight.

Imaging measurements were performed on a system which included a white light source (450-W Xe arc lamp, SLM Instruments, Inc., Urbana, Ill., Model FP-024), a monochromator for selection of the excitation wavelength (SLM Instruments, Inc., Model FP-092), and a CCD camera (Roper Scientific, Trenton, N.J., Model TE/CCD 1100 PF/UV, CCD chip size 1100×330 pixels). The monochromator was set at 470 nm (20 nm bandwidth) for the excitation of fluorescence of the array of analyte samples. Fluorescence from multiple sample regions was collected with the CCD camera through a long pass optical filter (Melles Gjiot, Inc., Irvine, Calif., Model 03FCG498 with a cut-off at 590 nm). The integration time to collect the images was 5 seconds.

Figure 6:
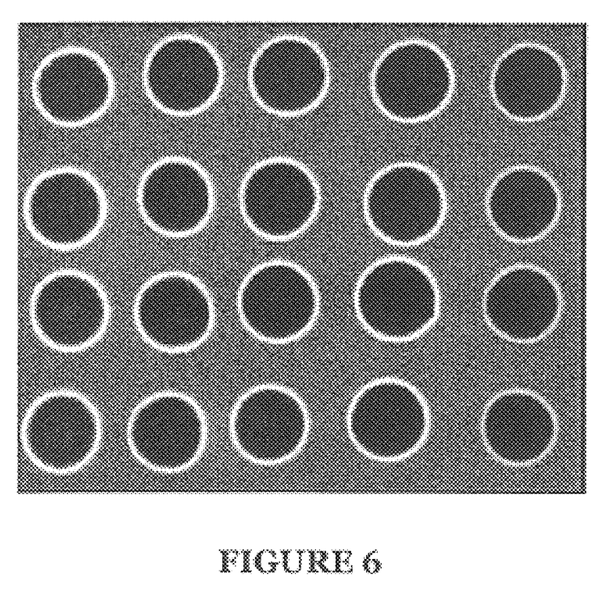
FIG. 6 is a fluorescence image of an analytical matrix after sample addition but before evaporation.

FIG. 6 shows the image of the array of droplets deposited onto the dye-modified support before the evaporation of the volatile components of the solutions. The image size was cropped down to 286×236 pixels. The 2 microliter volumes of BPA solutions were deposited as four replicate rows. The sequence of increasing BPA concentrations was from light to left.

Figure 7:
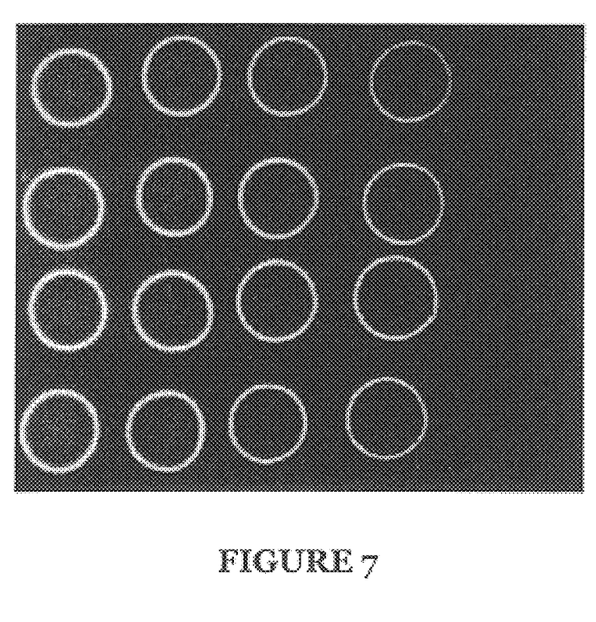
FIG. 7 is a fluorescence image of an analytical matrix after sample addition and evaporation.

FIG. 7 shows the fluorescence image of the analytical matrix after the evaporation of the volatile components of the solutions. Evaporation was performed at room temperature and atmospheric pressure.

Figure 8:
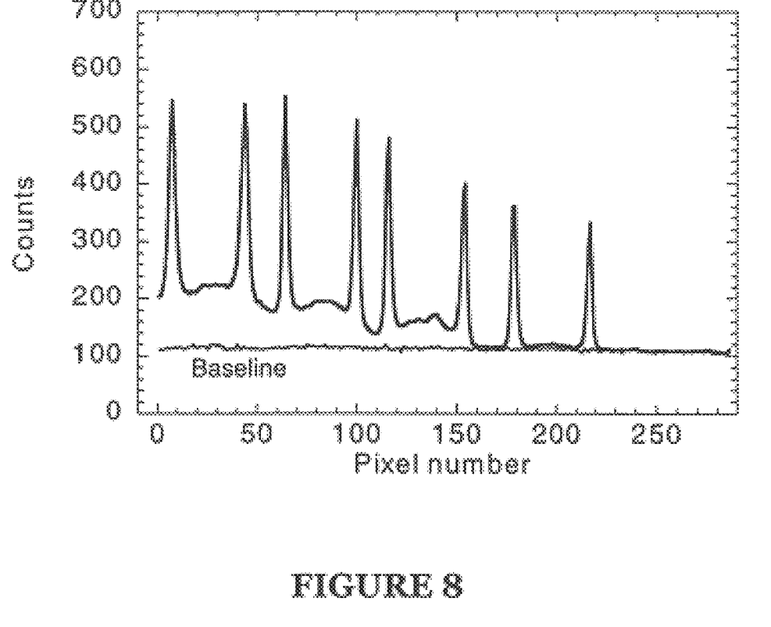
FIG. 8 is a plot of fluorescence intensity versus distance and corresponds to two cross sections through the image in FIG. 7, one (labeled baseline) corresponding to a line between rows of analytical sites, and the other corresponding to a line through the center of a row of analytical sites.

FIG. 8 shows two cross sections of FIG. 7. The baseline indicates a cross section through a portion of the image without BPA (i.e., between rows of analytical sites). The second profile line represents an average intensity of pixel rows 85–94 corresponding to the center of second row of BPA droplets from the bottom of the image. Fluorescence intensity of the deposited spots is proportional to BPA concentration in solution. This plot also illustrates the condensation of BPA around the edge of the spots.

Figure 9:
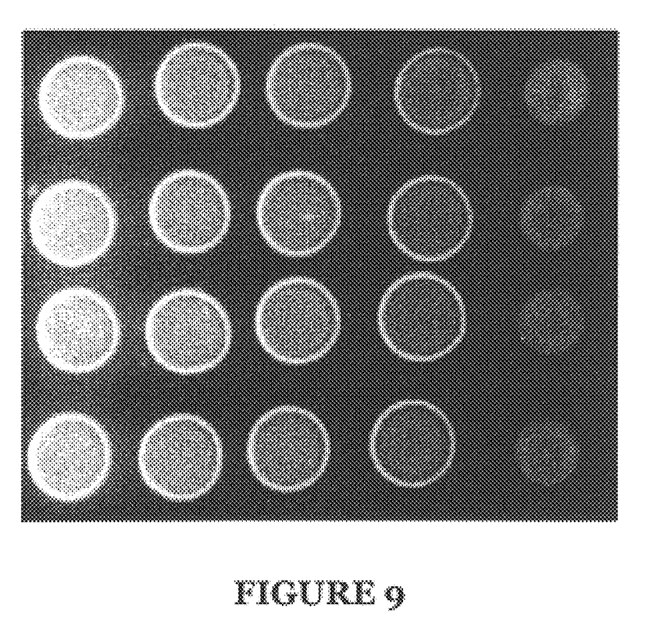
FIG. 9 is an image representing the ratio of fluorescence after and before the evaporation of the volatile components in the mixtures.

FIG. 9 depicts a ratio of fluorescence intensities after and before the evaporation of the volatile components in the mixtures. Clearly, the relative fluorescence intensity increased as a function of only the non-volatile fraction of the sample.

Figure 10:
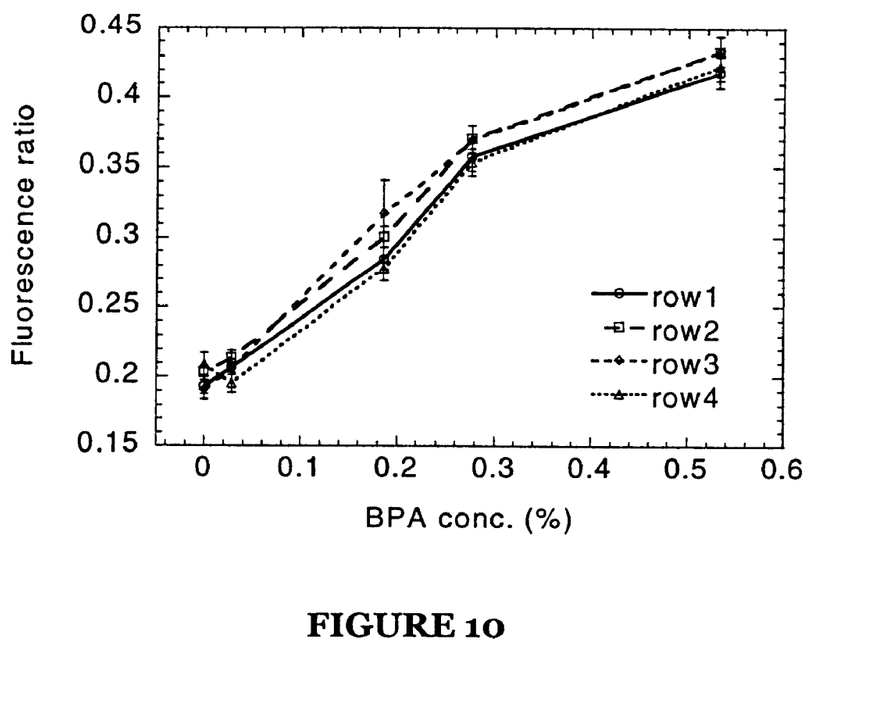
FIG. 10 is a plot of fluorescence ratio versus BPA concentration; each curve is derived from a different row of the sensor spots.

FIG. 10 presents four calibration curves constructed from the image in FIG. 9. Each curve is constructed for a different row of analytical sites. Each data point is the average of the fluorescence intensities of 64 pixels (8×8 pixel region) in the middle of the spots. The error bars represent one standard deviation from the mean values.

This example demonstrates rapid determination of analyte concentrations using an image of the entire matrix. It also demonstrates the small sample volumes required for this sensitive method.

In summary, the method provides a rapid means for parallel determination of analyte concentrations in a multitude of sample. The extreme sensitivity of the method means that only a very small amount of sample (e.g., 2 microliters) was needed for each analysis. A high dynamic range means that BPA concentrations ranging from 250 to 165,000 ppm can be accurately determined. The method's evaporation step removes interferences from volatile compounds such as phenol, acetone, acetonitrile, and water.

It will be understood that each of the elements described above, or two or more together, may also find utility in applications differing from the types described herein. While the invention has been illustrated and described as embodied in a method and system for rapid parallel determination of non-volatile analytes in complex combinatorial samples, it is not intended to be limited to the details shown, since various modifications and substitutions can be made without departing in any way from the spirit of the present invention. For example, additional analytical techniques can be used in concert with the present method and system when needed. Although many examples of various alternative chemicals, materials, and reaction components have been presented throughout this specification, the omission of a possible item is not intended to specifically exclude its use in or in connection with the claimed invention. As such, further modifications and equivalents of the invention herein disclosed may occur to persons skilled in the art using no more than routine experimentation, and all such modifications and equivalents are believed to be within the spirit and scope of the invention as defined by the following claims.

What is claimed is:

1. A method for analysis of at least one non-volatile analyte, comprising:
   providing a plurality of analytical samples comprising at least one non-volatile analyte for which the concentration is to be determined and at least one volatile component;
   providing an analytical matrix comprising a plurality of spatially differentiated analytical sites, each site comprising a sorbent material and a solvatochromic dye;
   delivering a known amount of each analytical sample onto at least one unique analytical site;
   subjecting the matrix to conditions effective to substantially evaporate the at least one volatile component of the analytical samples;
   irradiating a plurality of the analytical sites on the matrix with a first wavelength range;
   detecting a spectroscopic characteristic of the solvatochromic dye from each irradiated analytical site on the matrix with a second wavelength range; and
   determining a concentration of the non-volatile analyte at each irradiated analytical site based on the spectroscopic characteristic of the solvatochromic dye.

2. The method of claim 1, wherein the non-volatile analyte is a dihydric phenol.

3. The method of claim 2, wherein the non-volatile analyte is bisphenol A.

4. The method of claim 1, wherein the detection of a spectroscopic characteristic of the solvatochromic dye is accomplished with an array detector.

5. The method of claim 4, wherein the array detector comprises at least 25 detection sites for each analytical site.

6. A method for analysis of at least one non-volatile analyte, comprising:
   providing a plurality of analytical samples comprising at least one non-volatile analyte for which the concentration is to be determined and at least one volatile component;
   providing an analytical matrix comprising a plurality of spatially differentiated analytical sites, each site comprising a sorbent material and a solvatochromic dye;
   delivering a known amount of each analytical sample onto at least one unique analytical site;
   subjecting the matrix to conditions effective to substantially evaporate the at least one volatile component of the analytical samples;
   irradiating a plurality of the analytical sites on the matrix with a first wavelength range to stimulate fluorescence of the solvatochromic dye;
   detecting a fluorescence emission intensity of the solvatochromic dye from each analytical site on the matrix with a second wavelength range; and
   determining a concentration of the non-volatile analyte at each analytical site based on the fluorescence emission intensity of the solvatochromic dye.

7. The method of claim 6, wherein the fluorescence emission intensity of the solvatochromic dye in the second wavelength range is enhanced in the presence of the non-volatile analyte.

8. The method of claim 6, wherein the sorbent material comprises one or more of the group consisting of activated charcoal, silica, alumina, zeolites, diatomaceous earth and polymeric sorbents.

9. The method of claim 8, wherein the sorbent material comprises diatomaceous earth or silica.

10. The method of claim 8, wherein the polymeric sorbents are selected from the group consisting of poly(arylene ether) polymers, styrene divinylbenzene polymers, ethyl vinylbenzene polymers, divinyl benzene polymers, vinyl pyrrolidone polymers, vinyl pyridine polymers, polystyrene polymers, polyacrylonitrile polymers, poly(ethylene oxide) polymers, and cross-linked poly(acrylic ester) polymers.

11. The method of claim 6, wherein the solvatochromic dye comprises at least one dye selected from the group consisting of 4-dicyanmethylene-2-methyl-6-(p-methylaminostyryl)-4H-pyran, 6-propionyl-2-(dimethylamino)naphthalene and 9-(diethylamino)-5H-benzo[a]phenoxazin-5-one.

12. The method of claim 11, wherein the solvatochromic dye comprises 4-dicyanmethylene-2-methyl-6-(p-methylaminostyryl)-4H-pyran.

13. The method of claim 6, wherein the non-volatile analyte is a dihydric phenol.

14. The method of claim 13, wherein the non-volatile analyte is bisphenol A.

15. The method of claim 6, wherein the detection of fluorescence emission is accomplished with an array detector.

16. The method of claim 15, wherein the array detector comprises at least 25 detection sites for each analytical site.

17. The method of claim 6, wherein the known amount of each analytical sample is about 0.1 to about 100 microliters.

18. The method of claim 17, wherein the known amount of each analytical sample is about 1 to about 50 microliters.

19. The method of claim 1, wherein the known amount of each analytical sample is delivered onto at least two analytical sites.

20. The method of claim 6, wherein the fluorescence emission intensity is essentially independent of the known amount of analytical sample.

21. A method for analysis of bisphenol A, comprising:
   providing a plurality of analytical samples comprising bisphenol A and at least one volatile component;
   providing an analytical matrix comprising a plurality of spatially differentiated analytical sites, each site comprising a diatomaceous earth sorbent material and 4-dicyanmethylene-2-methyl-6-(p-methylaminostyryl)-4H-pyran;

delivering a known amount of each analytical sample onto at least one unique analytical site;

subjecting the matrix to conditions effective to substantially evaporate the at least one volatile component of the analytical samples;

irradiating a plurality of the analytical sites on the matrix at about 480 to about 515 nm to stimulate fluorescence of the solvatochromic dye;

detecting a fluorescence emission intensity from each analytical site on the matrix at about 530 to about 600 nm; and determining a concentration of bisphenol A in each analytical sample based on the fluorescence emission intensity from each analytical site.

22. A system for analysis of at least one non-volatile analyte, comprising:

a plurality of analytical samples comprising at least one non-volatile analyte for which the concentration is to be determined and at least one volatile component;

an analytical matrix comprising a plurality of spatially differentiated analytical sites, each site comprising a sorbent material and a solvatochromic dye;

a sample loader for delivering a known amount of each analytical sample onto at least one unique analytical site;

an evaporator for expediting the evaporation of at the at least one volatile component of the analytical samples;

a light source for irradiating a plurality of the analytical sites on the matrix with a first wavelength range;

a detector for detecting a spectroscopic characteristic of the solvatochromic dye from each analytical site on the matrix with a second wavelength range; and a computer for determining a concentration of the non-volatile analyte at each analytical site based on the spectroscopic characteristic of the solvatochromic dye, and, optionally, for responsively controlling one or more of the sample loader, the evaporator, the light source, and the detector.

23. A system for analysis of at least one non-volatile analyte, comprising:

a plurality of analytical samples comprising at least one non-volatile analyte for which the concentration is to be determined and at least one volatile component;

an analytical matrix comprising a plurality of spatially differentiated analytical sites, each site comprising a sorbent material and a solvatochromic dye;

a sample loader for delivering an amount of each analytical sample onto at least one unique analytical site;

an evaporator for expediting the evaporation of at the at least one volatile component of the analytical samples;

a light source for irradiating all analytical sites on the matrix with a first wavelength range to stimulate fluorescence of the solvatochromic dye;

a detector for detecting a fluorescence emission intensity of the solvatochromic dye from each analytical site on the matrix with a second wavelength range; and a computer for determining a concentration of the non-volatile analyte at each analytical site based on the fluorescence emission intensity of the solvatochromic dye, and, optionally, for responsively controlling one or more of the sample loader, the evaporator, the light source, and the detector.

* * * * *